(12) United States Patent
Oguri

(10) Patent No.: US 8,202,478 B2
(45) Date of Patent: Jun. 19, 2012

(54) OBSERVATION APPARATUS

(75) Inventor: Kazumasa Oguri, Yokosuka (JP)

(73) Assignee: Japan Agency for Marine-Earth Science & Technology, Yokosuka-shi, Kanagawa (JP)

( * ) Notice: Subject to any disclaimer, the term of this patent is extended or adjusted under 35 U.S.C. 154(b) by 220 days.

(21) Appl. No.: 12/398,526

(22) Filed: Mar. 5, 2009

(65) Prior Publication Data

US 2009/0224159 A1 Sep. 10, 2009

(30) Foreign Application Priority Data

Mar. 5, 2008 (JP) ................................. 2008-054891

(51) Int. Cl.
*G01N 33/00* (2006.01)
(52) U.S. Cl. ................. 422/82.05; 422/82.06; 422/68.1; 422/500; 422/547
(58) Field of Classification Search .................. 422/68.1, 422/82.05, 82.06, 500, 547
See application file for complete search history.

(56) References Cited

U.S. PATENT DOCUMENTS

| 3,588,512 | A | | 6/1971 | Hollien |
| 4,096,466 | A | | 6/1978 | Johnson |
| 5,708,957 | A | * | 1/1998 | Chuang et al. ............. 422/82.07 |
| 2005/0247863 | A1 | | 11/2005 | Kaessner |

FOREIGN PATENT DOCUMENTS

JP 2007-120992 A 5/2007

OTHER PUBLICATIONS

European Search Report dated Feb. 2, 2011, issued in corresponding European Patent Application No. 09153416.
Glud et al., "Distribution of oxygen in surface sediments from central Sagami Bay, Japan: In situ measurements by microelectrodes and planar optodes", Deep-Sea Research. Part 1. Oceanographic Research Papers, Pergamon Press, Oxford, GB, vol. 52, No. 10, Oct. 1, 2005, pp. 1974-1987, XP005043677.
Oguri et al., "In situ measurement of time-series two dimensional O2 distributions at sediment-water interface using a planar O2 optode system connected with a submarine cable", Underwater Technology and Workshop on Scientific Use of Submarine CABL ES and Related Technologies, 2007. Symposium on, IEEE, PI, Apr. 1, 2007, pp. 367-370, XP031176131.
European Office Action dated Oct. 27, 2011, issued in corresponding European Patent Application No. 09153416.4.

* cited by examiner

*Primary Examiner* — Sam P Siefke
(74) *Attorney, Agent, or Firm* — Westerman, Hattori, Daniels & Adrian, LLP

(57) ABSTRACT

An observation apparatus can observe the temporal fluctuations of the two-dimensional distribution of oxygen concentration in the bottom sludge and also in the bottom water on the seabed at an observation site. The observation apparatus includes a pressure-resistant container main body section that has a pressure-resistant window and is hermetically sealed by a pressure-resistant container closure section, a sensor foil that contains an oxygen quenching material and is arranged at the pressure-resistant window, an excitation light source that is arranged at the pressure-resistant container main body section to irradiate the sensor foil and an image pickup apparatus that shoots the sensor foil.

5 Claims, 12 Drawing Sheets

OBSERVATION APPARATUS

CROSS REFERENCE TO RELATED APPLICATION

This application is based upon and claims the benefit of priority from the prior Japanese Patent Application No. 2008-54891, filed on Mar. 5, 2008, the entire contents of which are incorporated herein by reference.

BACKGROUND OF THE INVENTION

1. Field of the Invention

The present invention relates to an observation apparatus for visualizing the temporal fluctuations of the oxygen concentration distribution along the boundary of the bottom sludge and the bottom water on the seabed for observation.

2. Description of the Related Art

The dissolved oxygen level on the surface of the bottom sludge on the seabed takes a vital role for maintaining a sound ecosystem on the seabed. Known techniques for looking into the dissolved oxygen level on the surface of the bottom sludge include one with which a container having an oxygen concentration measuring chamber with an oxygen electrode, which is also called a bulging chamber, is dropped to the seabed of an observation site to measure the fall, if any, in the oxygen concentration level at the site.

JP-A-2007-120992 discloses a seabed oxygen concentration measuring apparatus having an oxygen concentration measuring chamber formed by arranging a transparent disk on a plurality of pillars standing on a construction frame so as to make the transparent disk operate as top plate of the oxygen concentration measuring chamber and fitting an optical dissolved oxygen meter for measuring the dissolved oxygen level in the oxygen concentration measuring chamber and an agitation device for agitating the internal air of the chamber to the transparent disk.

SUMMARY OF THE INVENTION

However, the known apparatus is designed to put a cover on the seabed for the measurement so that it is accompanied by a problem that it cannot catch the temporal change, if any, in the oxygen concentration distribution in the bottom sludge on the seabed nor in the seawater. It is also accompanied by a problem that the two-dimensional distribution of oxygen concentration cannot be observed by means of an electrode in the bottom sludge on the seabed nor in the seawater.

According to a first aspect of the present invention, the above-identified problems are dissolved by providing an observation apparatus including: a pressure-resistant container main body section that has a pressure-resistant window and is hermetically sealed by a pressure-resistant container closure section; a sensor foil that contains an oxygen quenching material and is arranged at the pressure-resistant window; an excitation light source that is arranged at the pressure-resistant container main body section to irradiate the sensor foil; and an image pickup apparatus that shoots the sensor foil.

According to a second aspect of the present invention, in the observation apparatus as defined above, a switch is arranged on the outer periphery of the pressure-resistant container main body section and an observation sequence is started by the switch.

According to a third aspect of the present invention, in the observation apparatus as defined above, a control circuit is arranged in the inside of the pressure-resistant container main body section to control the excitation light source and the image pickup apparatus.

According to a fourth aspect of the present invention, in the observation apparatus as defined above, a main switch is arranged in the inside of the pressure-resistant container main body section to turn on and off the power supply to the control circuit.

Thus, the observation apparatus according to the present invention can observe the temporal fluctuations of the two-dimensional distribution of oxygen concentration in the bottom sludge on the seabed and also in the seawater.

DETAILED DESCRIPTION OF THE PREFERRED EMBODIMENTS

Figure 1:
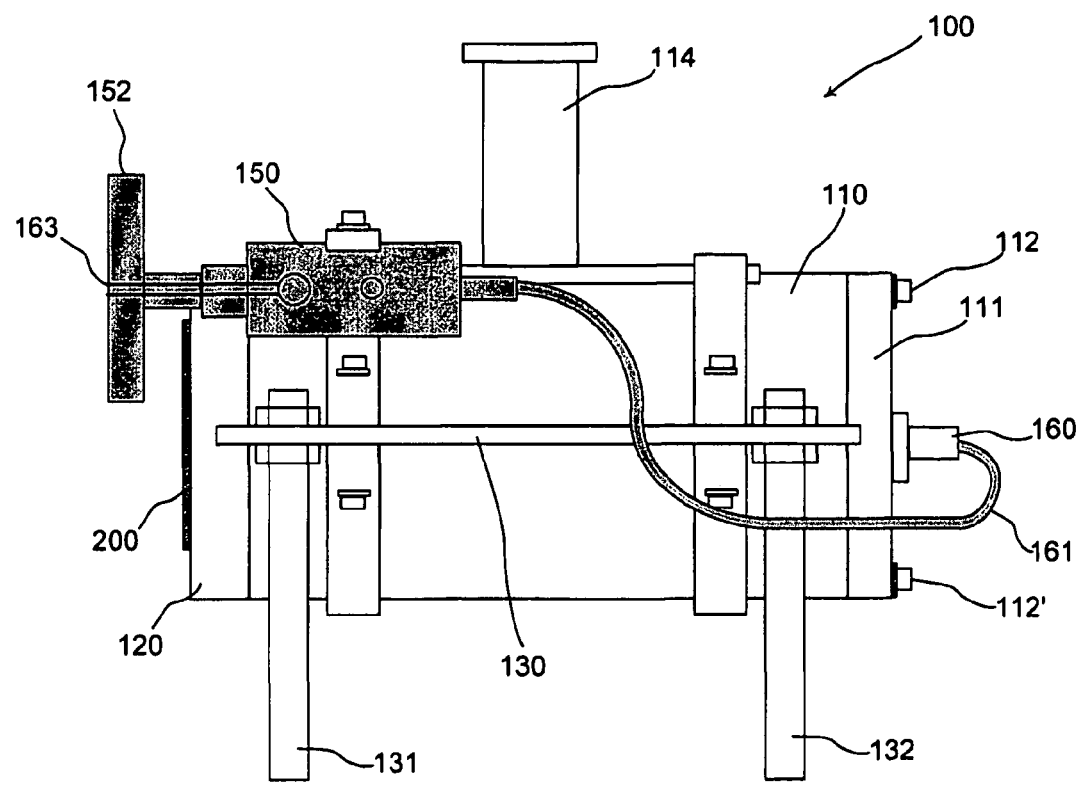
FIG. 1 is a schematic lateral view of an observation apparatus according to an embodiment of the present invention.
Figure 2:
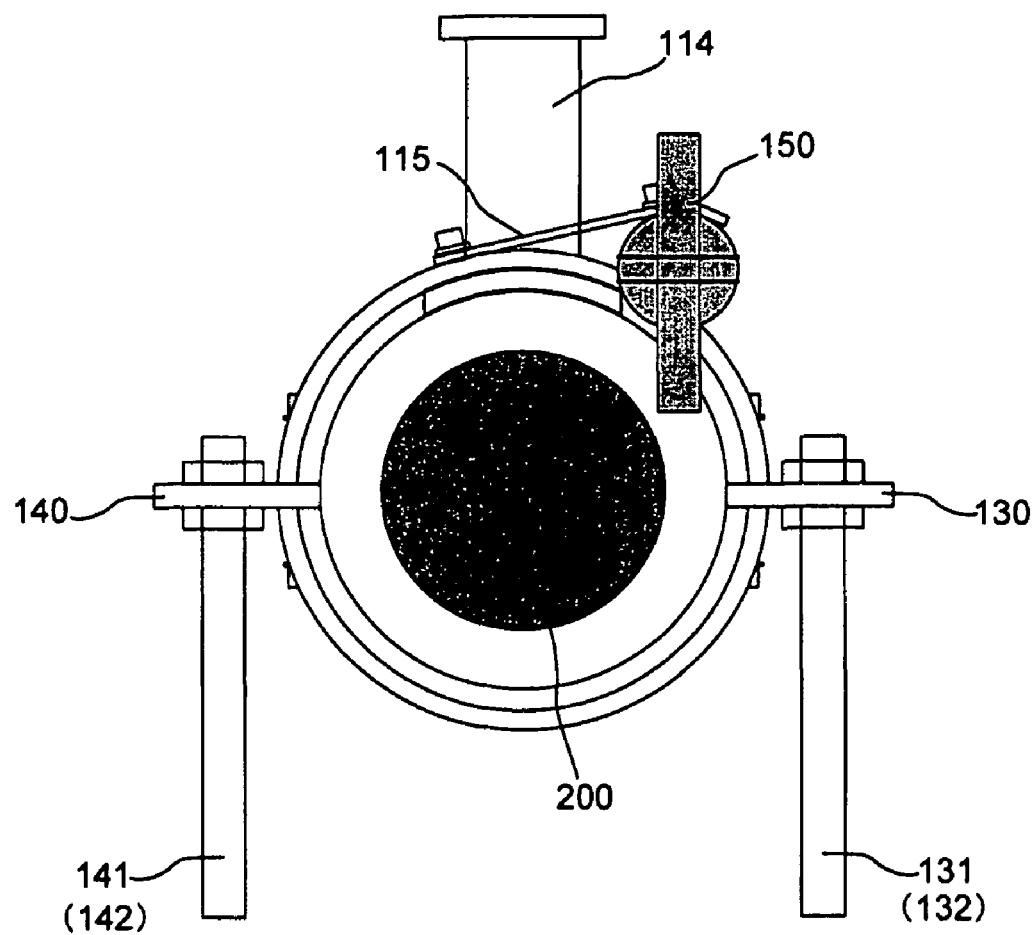
FIG. 2 is a schematic front view of the observation apparatus according to the embodiment of the present invention.
Figure 3:
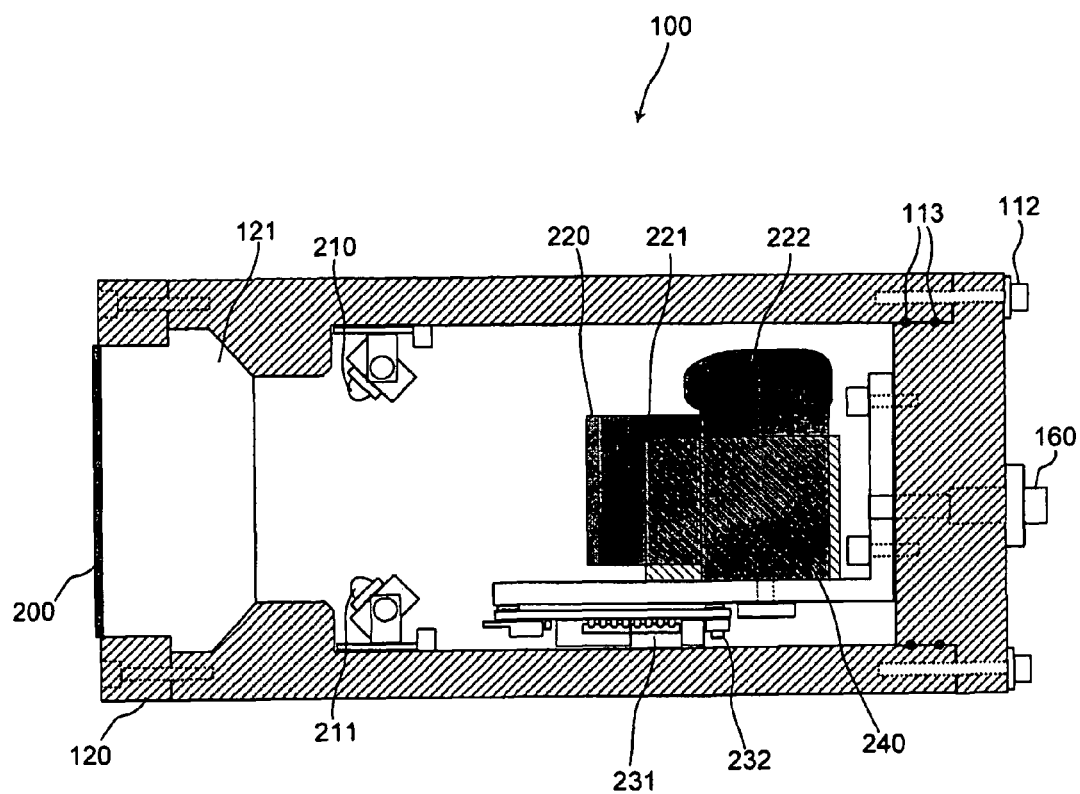
FIG. 3 is a schematic illustration of the configuration of the inside of the pressure-resistant container of the observation apparatus according to the embodiment of the present invention.

Now, preferred embodiments of the present invention will be described in greater detail by referring to the accompanying drawings. FIG. 1 is a schematic lateral view of an observation apparatus according to the embodiment of the present invention. FIG. 2 is a schematic front view of the observation apparatus according to the embodiment of the present invention. FIG. 3 is a schematic illustration of the configuration of the inside of the pressure-resistant container of the observation apparatus according to the embodiment of the present invention. Referring to FIGS. 1 through 3, 100 denotes the observation apparatus, 110 denotes the pressure-resistant container main body section of the apparatus and 111 denotes the pressure-resistant container closure section while 112, 112' denote so many bolts, 113 denotes an O ring and 114, 115, respectively denote a handle section and a photoswitch fitting member. Reference numerals 120, 121 respectively denote a pressure-resistant window section and a pressure-resistant glass panel, 130, 131 and 132 respectively denote a leg fitting member, a first leg section and a second leg section and 140, 141 and 142 respectively denote another leg fitting member, a third leg section and a fourth leg section, while 150 and 152 respectively denote a photoswitch and a pin, 160, 161 and 163 respectively denote an underwater connector, a cable and an annular elastic body and 200 denotes a sensor foil. Reference numerals 210 and 211 denote so many excitation light sources and 220, 221 and 222 respectively denote a filter, a lens section and an image pickup apparatus, while 231 and 232 respectively denote a control circuit substrate and a main switch and 240 denotes a power supply section.

Now, the embodiment of the observation apparatus 100 according to the present invention will be described below on a basic assumption that it is placed in position at the boundary of the bottom sludge and the bottom water in a deep sea of about 1,000 m to 2,000 m by means of a submarine and the two-dimensional distribution of oxygen concentration is observed along with the temporal fluctuations thereof. However, the observation apparatus 100 according to the present invention can find applications in various geographical areas including lakes, swamps and rivers. In other words, the observation apparatus 100 according to the present invention can find applications in any geographical areas for surveying the oxygen concentration distribution.

The observation apparatus 100 is designed to produce a hermetically sealed space in the inside thereof by means of a hollow and cylindrical pressure-resistant container main body section 110 that is made of stainless steel, a pressure-resistant container closure section 111 and a pressure-resistant window section 120, the closure section 111 and the window section 120 being arranged at the opposite ends of the main body section 110. The pressure-resistant container closure section 111 is removably fitted to the main body section 110. An O-ring 113 is arranged between the pressure-resistant container main body section 110 and the pressure-resistant container closure section 111 to make the observation apparatus 100 watertight. The pressure-resistant container main body section 110 and the pressure-resistant container closure section 111 are rigidly fitted to each other by means of screw bolts 112, 112'.

When operating the observation apparatus 100 according to the present invention for observation, the pressure-resistant container closure section 111 is once removed from the pressure-resistant container main body section 110 and the arrangement necessary for the observation is set in position in the internal space of the pressure-resistant container main body section 110. Then, the observation apparatus 100 is placed in position at the underwater observation point. After the completion of the observation, the observation apparatus 100 is drawn up from the sea and the pressure-resistant container closure section 111 is removed. Then, the arrangement in the inside is taken out to retrieve the acquired data.

The handle section 114 arranged on the pressure-resistant container main body section 110 is to provide a good handleability when placing the observation apparatus 100 in position at a desired point of observation. The leg fitting member 130 where the first leg section 131 and the second leg section 132 are fitted and the other leg fitting member 140 where the third leg section 141 and the fourth leg section 142 are fitted are arranged at the opposite lateral sides of the pressure-resistant container main body section 110. Due to the first leg section 131, the second leg section 132, the third leg section 141 and the fourth leg section 142, the observation apparatus 100 would not be buried in bottom sludge when the observation apparatus 100 is placed in position on the bottom sludge of a deep sea. In other words, the observation apparatus 100 remains near the boundary of the bottom sludge and the bottom water so that it can observe temporal fluctuations of the two-dimensional distribution of oxygen concentration at the boundary of the bottom sludge and the bottom water.

The pressure-resistant glass panel 121 is fitted to the pressure-resistant window section 120 arranged at one of the opposite ends of the pressure-resistant container main body section 110 of the observation apparatus 100 to allow an observer to observe the outside of the pressure-resistant container main body section 110 from the inside of the pressure-resistant container main body section 110. The sensor foil 200 is fitted to the pressure-resistant window section 120 at the outside of the latter. The distribution of oxygen concentration is visualized by means of this sensor foil 200 of the observation apparatus 100 according to the present invention and a visualized image of the distribution of oxygen concentration can be picked up at appropriate time intervals by means of the image pickup apparatus 222 set in the inside of the pressure-resistant container main body section 110.

The sensor foil 200 is prepared by forming a thin film of an oxygen quenching material on a transparent resin film that is typically a PET film and applying black silicon resin to the surface of the thin film of the oxygen quenching material. The oxygen quenching material contains a pigment that emits light when exposed to excitation light and an oxygen permeable binder. The black silicon resin allows oxygen dissolved in sludge and in seawater to permeate itself. The sensor foil 200 is fitted to the pressure-resistant window section 120 at the transparent resin film side thereof so as to completely cover the pressure-resistant window section 120 and allow the black silicon resin side to contact sludge and seawater that are objects of observation.

The pigment contained in the oxygen quenching material may typically be a metal porphyrin such as platinum porphyrin or a transition metal complex such as ruthenium complex. As excitation light is irradiated to such a pigment, the pigment molecules are driven to move into an excited state and the pigment molecules in an excited state (excited pigment molecules) emit luminescent light (fluorescent light, phosphorescent light) having a wavelength longer than the wavelength of excitation light. However, if oxygen molecules exist around the excited molecules, the excited molecules are deprived of energy by the oxygen molecules to give rise to a quenching phenomenon in proportion to the probability of collision of the oxygen molecules and the excited molecules. In other words, the intensity of light emitted by the pigment will increase or decrease as a function of the oxygen concentration in the atmosphere surrounding the pigment. The observation apparatus 100 according to the present invention can pick up an image of the intensity of emitted light typically by means of an image pickup apparatus and measure the oxygen concentration around the pigment.

For this embodiment, the sensor foil 200 is prepared by dropping a toluene solution where PtOEP (platinum porphyrin) and polystyrene pellets are dissolved onto a 100 μm-thick PET film to form a thin film and applying black silicon resin to the surface of the thin film by knife coating.

Pigments containing an oxygen quenching material that can be used for the purpose of the present invention are not subjected to any particular limitation so long as the pigment emits light such as fluorescent light or phosphorescent light when emitted with excitation light and indicates oxygen quenching properties. Examples of pigments that can be used for the purpose of the present invention include metal porphyrin complexes such as platinum porphyrin that may be platinum octaethyl porphyrin or platinum tetrapentafluorophenyl porphyrin, transition metal complexes such as phenanthroline ruthenium chloride, polycyclic aromatic compounds such as pyrene and perylene and derivatives of polycyclic aromatic compounds. Particularly, the use of platinum tetrapentafluorophenyl porphyrin or phenanthroline ruthenium chloride is preferable from the viewpoint of emission life, emission intensity and thermal stability.

The photoswitch 150 is operated to trigger a real observation sequence of the observation apparatus 100. It is fitted to the pressure-resistant container main body section 110 at the outside of the latter by means of the photoswitch fitting member 115. The photoswitch 150 is designed so as to operate as trigger when the pin 152 inserted into the main body section of the photoswitch 150 is pulled out from the main body section. The pin 152 is held in the state of being inserted into the main body section side of the photoswitch 150 by the elastic force of the annular elastic body 163 so as not to come out from the main body section of the photoswitch 150 until the observation apparatus 100 according to the present invention is placed in position at the point of observation.

Instead of the system of arranging a light emitting element such as a light emitting diode and a light receiving element such as a phototransistor as trigger for the switch so that light hits the light receiving element to make the control circuit start operating as the pin is pulled out, a system where a magnet is fitted to the pin and a magnetic switch is turned on when the pin is pulled out or a plug type switch available from Seacon may alternatively be employed for the purpose of the present invention.

As the observation apparatus 100 is placed in position at the point of observation, the annular elastic body 163 is taken out and the pin 152 is pulled out from the main body section of the photoswitch 150 by a diver/operator or by means of a manipulator of a submarine. Then, as a result, an observation sequence is started under the control of the control circuit contained in the pressure-resistant container main body section 110 of the observation apparatus 100.

The space in the inside of the pressure-resistant container main body section 110 of the observation apparatus 100 is limited. In other words, the space for arranging the power supply section 240 for supplying power to the image pickup apparatus 222 and the control circuit is limited. Therefore, the capacity of the power supply that can be used for observations is limited. However, the observation apparatus 100 according to the present invention is so designed that it is triggered to start an observation sequence by the photoswitch 150 after the observation apparatus 100 is placed in position at a point of observation so that the limited capacity of the power supply can be efficiently exploited for the observation sequence.

The cable 161 is connected to the photoswitch 150 at an end and to the underwater connector 160 at the other end thereof. An electric connection is established between the photoswitch 150 and the control circuit and other related components contained in the pressure-resistant container main body section 110 as the underwater connector 160 is brought into engagement with the underwater connector provided at the side of the pressure-resistant container closure section 111.

Now, the configuration of the control circuit and that of the image pickup apparatus contained in the inside of the pressure-resistant container main body section 110 will be described mainly referring to FIG. 3. The pressure-resistant glass panel 121 of the pressure-resistant window section 120 is a transparent glass panel that is highly pressure-resistant so that the operator can observe the sensor foil 200 fitted to the pressure-resistant glass panel 121 from the inside of the pressure-resistant container main body section 110. The execution light sources 210, 211 are light sources for irradiating excitation light to the sensor foil 200 fitted to the pressure-resistant glass panel 121. When a material prepared by using platinum octaethyl porphyrin is employed as oxygen quenching material, ultraviolet LEDs (Model NCCU001E available from NICHIA Corporation), of which center of the emission wavelength is in the vicinity of 380 nm, maybe used for the excitation light sources 210, 211. As the sensor foil 200 is irradiated with excitation light by the execution light sources 210, 211, the oxygen quenching material contained in the sensor foil 200 is driven to move into an excited state (to become excited molecules) and subsequently emit luminescent light (fluorescent light, phosphorescent light) having a wavelength longer than that of excitation light when the oxygen quenching material moves back into a ground state. However, if oxygen molecules exist around the excited molecules, the excited molecules are deprived of energy by the oxygen molecules to give rise to a quenching phenomenon in proportion to the probability of collision of the oxygen molecules and the excited molecules. Due to the phenomenon, luminescent light (fluorescent light, phosphorescent light) shows variances in the intensity in accordance with the spots where no oxygen molecules exist and the spots where oxygen molecules exist along the plane where the sensor foil 200 extends. The two-dimensional distribution of oxygen concentration can be observed in the bottom sludge and also in the seawater by picking up an image of the variances by means of the image pickup apparatus 222. As the image pickup apparatus 222 is operated for imaging at regular time intervals, it is possible to observe the temporal fluctuations of the oxygen concentration distribution in the sludge and also in the seawater.

The filter 220 transmits luminescent light emitted from the oxygen quenching material. It is fitted to the front end of the lens section 221 of the image pickup apparatus 222. In this embodiment, a digital single-lens reflex camera (Model EOS 30D: available from Canon) and a macro lens (Model EF50 mm F2.5: available from Canon) are employed respectively for the image pickup apparatus 222 and the lens section 221, while a red filter is employed for the filter 220.

Since the observation apparatus 100 according to the present invention needs to be adapted to pick up an image of luminescent light from the sensor foil 200, any light other than the luminescent light has to be blocked so as not to strike the sensor foil 200. For this reason, when the surface area of the sensor foil 200 and that of the pressure-resistant window section 120 do not agree with each other and light can strike the area of the difference between the surface area of the sensor foil 200 and that of the pressure-resistant window section 120, the area of the difference needs to be masked by a black tape or the like so as to prevent external light from entering the pressure-resistant container. Preferably, the inside of the pressure-resistant container including that of the pressure-resistant container main body section 110 and that of the pressure-resistant container closure section 111 is painted black to prevent internal reflections from taking place. When the image pickup apparatus 222 is provided with an indicator lamp, the lamp is preferably masked by means of a black tape.

The control circuit substrate 231 is a substrate where the control circuit for controlling the execution light sources 210, 211 and the image pickup apparatus 222 among others is mounted. The photoswitch 150 is made to operate as trigger for starting an observation sequence of the observation apparatus 100 according to the present invention. The main switch 232 is a switch for starting the photoswitch 150 itself. The main switch 232 may typically be arranged on the control circuit substrate 231. The power supply section 240 is a battery for supplying power to the image pickup apparatus 222 and the control circuit arranged on the control circuit substrate 231.

Figure 4:
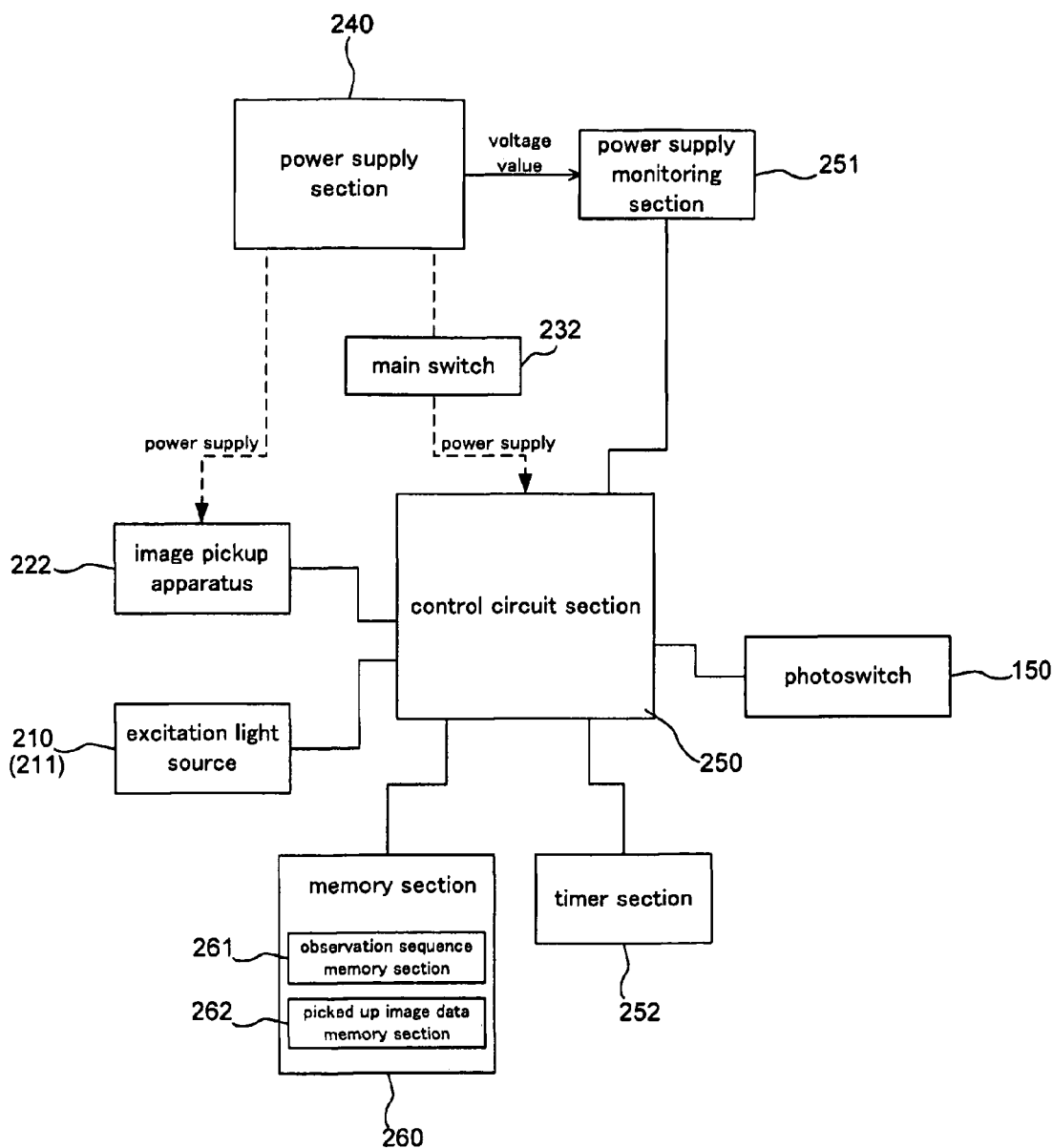
FIG. 4 is a schematic block diagram of the observation apparatus according to the embodiment of the present invention.

Now, the control circuit of the observation apparatus 100 will be described below in greater detail. FIG. 4 is a schematic block diagram of the observation apparatus according to the embodiment. Referring to FIG. 4, reference numerals 150, 210 and 211 respectively denote the photoswitch and the excitation light sources, 222 and 232 respectively denote the image pickup apparatus and the main switch and 240 and 250 respectively denote the power supply section and the control circuit section, while 251 and 252 respectively denote a power supply monitoring section and timer section and 260, 261 and 262 respectively denote a memory section, an observation sequence memory section (for storing the imaging time intervals, the exposure time and so on) and a picked up image data memory section.

The power supply section 240 supplies power to the control circuit section 250 and the image pickup apparatus 222. The power supply section 240 is monitored by the power supply monitoring section 251 for the voltage value thereof, for instance. The outcome of the monitoring operation of the power supply monitoring section 251 is input to the control circuit section 250.

The main switch 232 is turned on or off so as to supply power to the control circuit control section 250 or block the power supply, whichever appropriate.

The control circuit section 250 is typically formed by a microcomputer, an interface means for connecting the microcomputer and other components, an input unit for specifying an observation sequence and so on. The control circuit section 250 is driven to operate according to a program stored in the memory section 260.

The photoswitch 150 includes a light emitting element and a light receiving element that are not shown in FIG. 4. It is turned off when the light path between the light emitting element and the light receiving element is blocked and turned on when the light receiving element receives light from the light emitting element. The operation of the photoswitch 150 can be controlled by the control circuit section 250.

The excitation light sources 210, 211 are controlled by the control circuit section 250 to flash. If necessary, it may be so arranged that power is supplied to the excitation light sources 210, 211 from the power supply section 240. The timer section 252 is arranged to count time in order to provide a basis for managing the observation sequence to be followed by the observation apparatus 100.

The memory section 260 stores the program for operating the control circuit section 250 and also provides a work area for the control circuit section 250. According to the present invention, the memory section 260 includes an area for an observation sequence (the imaging time intervals, the exposure time, the number of times of imaging, the timing of flashing the excitation light sources, etc.) memory section 261 and an area for the picked up image data memory section 262.

The observation sequence memory section 261 stores an observation sequence of the observation apparatus 100. An observation sequence shows the timing at which the excitation light sources 210, 211 are flashed, how the image pickup apparatus 222 picks up an image in response (what will be the exposure time and the aperture value), how many times the image pickup apparatus 222 shoot in a shooting session, what is the standby time until the next shooting session, how many times the image pickup apparatus 222 shoot in the overall observation sequence and so on. The simplest sequence may show the shooting intervals and the exposure time of the image pickup apparatus 222 and the timing at which the excitation light sources 210, 211 are flashed. The observation sequence stored in the observation sequence memory section 261 may be rewritten whenever necessary or altered by operating the input unit of the control circuit section 250.

The picked up image data memory section 262 stores the picked up image data stored once in the image pickup apparatus 222. The picked up image data stored in the picked up image data memory section 262 can be taken out to the outside by way of an appropriate interface means. Thus, the picked up image data can be obtained from the observation apparatus 100 after the end of the observation on the seabed.

If the image pickup apparatus 222 is provided with an appropriate memory device for storing picked up image data, the memory section 260 may not necessarily have to have the picked up image data memory section 262.

Figure 5:
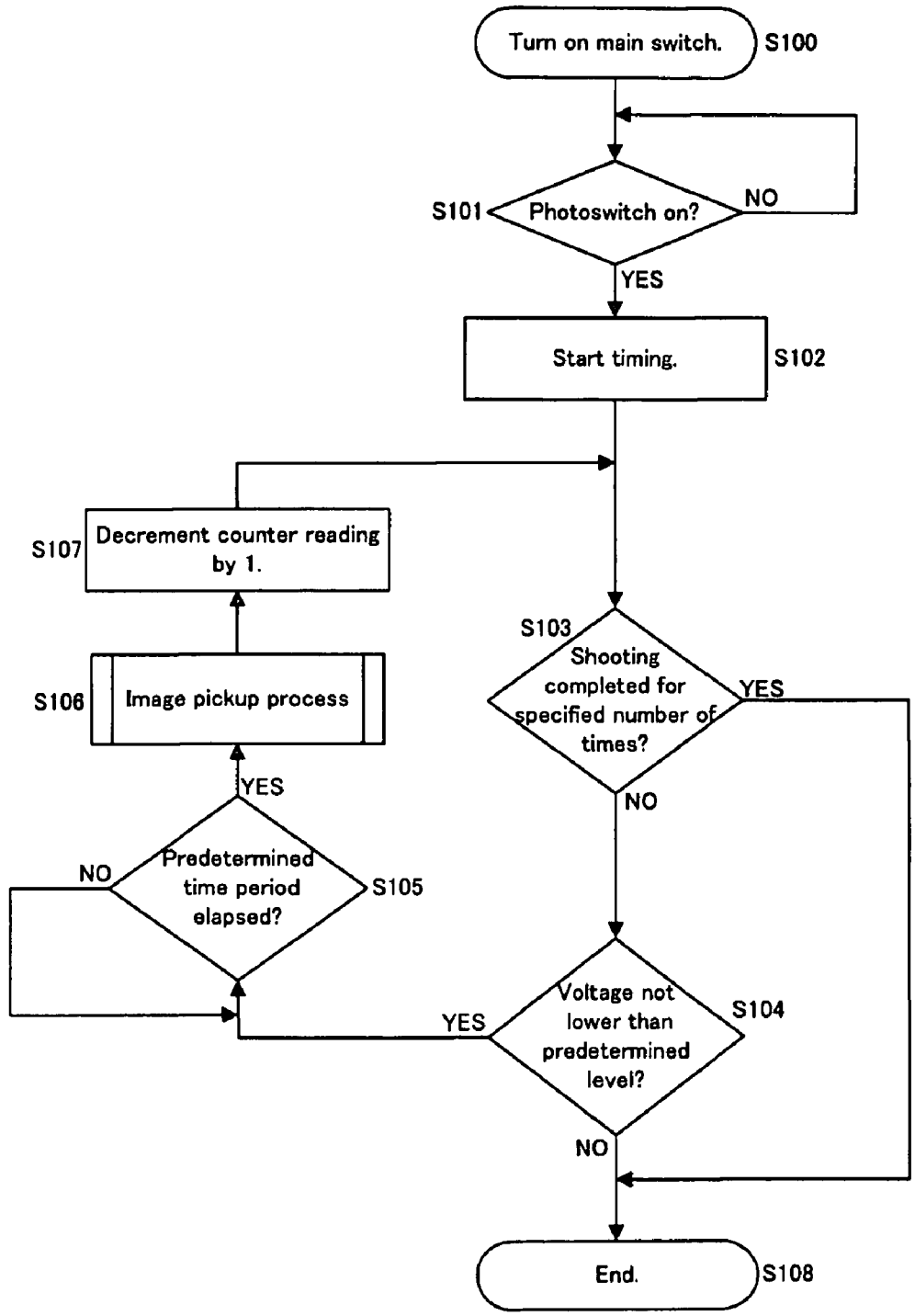
FIG. 5 is a flowchart of the process of the control circuit of the observation apparatus according to the embodiment of the present invention.
Figure 6:
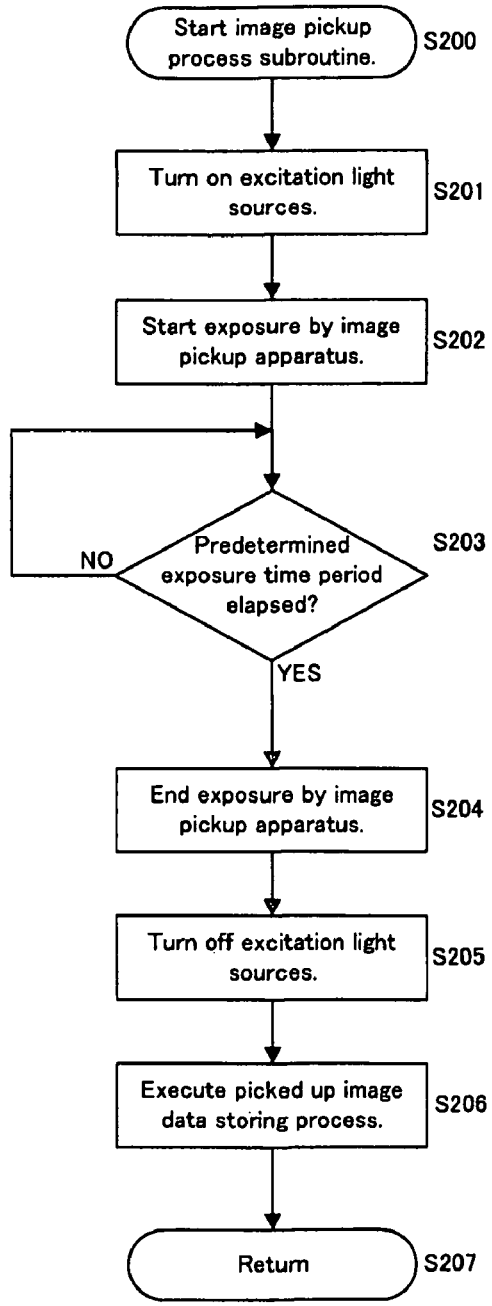
FIG. 6 is a flowchart of the image pickup process subroutine of the control circuit of the observation apparatus according to the embodiment of the present invention.
Figure 7A:
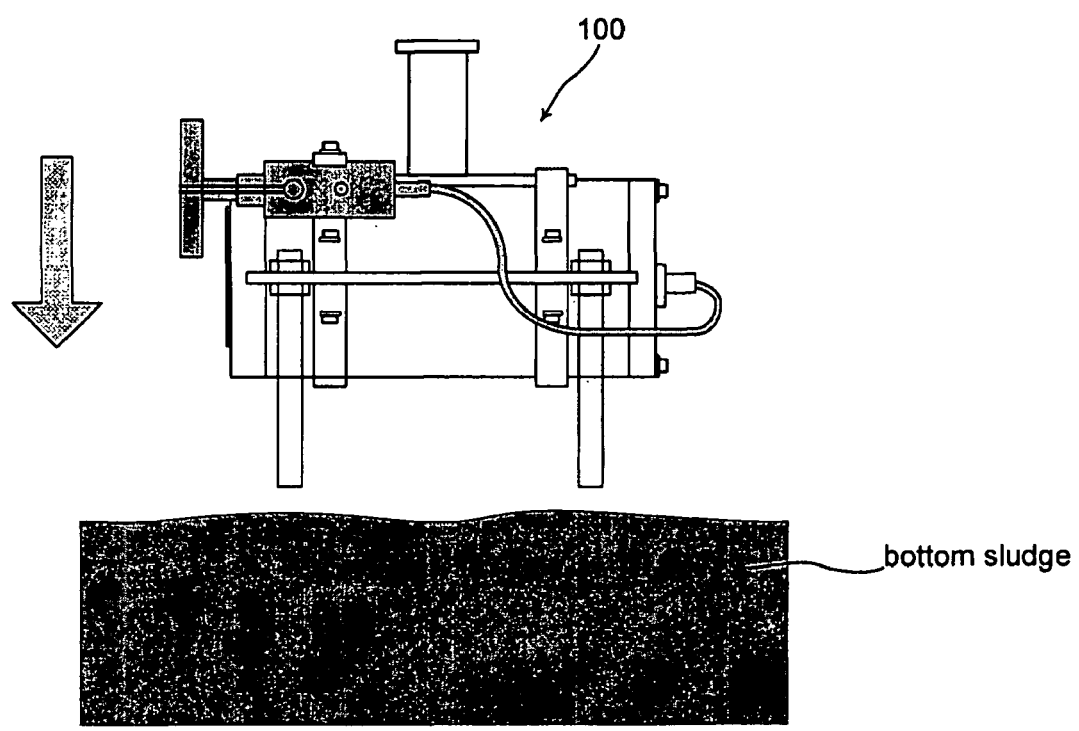
FIG. 7A is a schematic illustration of an operation step of placing the observation apparatus according to the embodiment of the present invention at a point of observation.
Figure 7B:
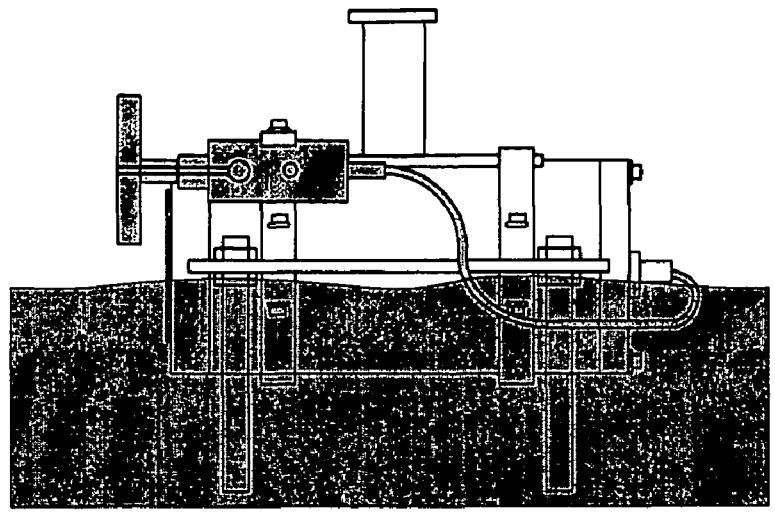
FIG. 7B is a schematic illustration of another operation step of placing the observation apparatus according to the embodiment of the present invention at the point of observation.
Figure 7C:
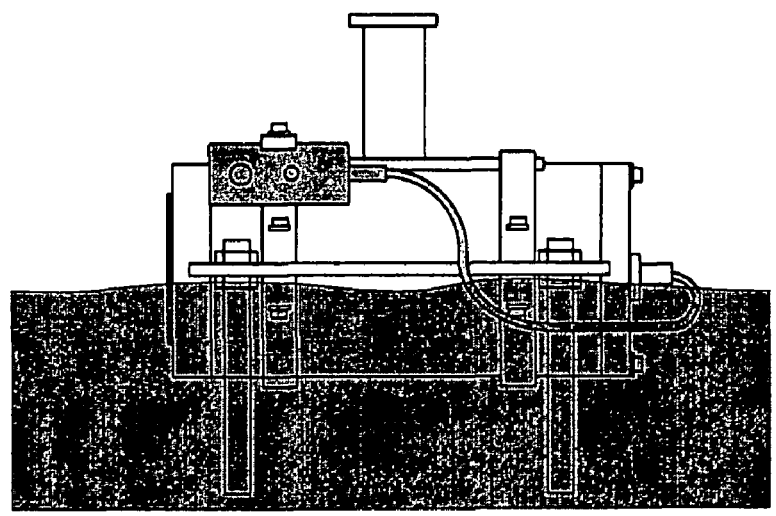
FIG. 7C is a schematic illustration of still another operation step of placing the observation apparatus according to the embodiment of the present invention at the point of observation.

Now, the flow of placing the observation apparatus 100 in position and that of the process to be executed by the control circuit section 250 will be described below. FIG. 5 is a flowchart of the control process of the control circuit of the observation apparatus according to the embodiment. FIG. 6 is a flowchart of the image pickup process subroutine of the control circuit of the observation apparatus according to the embodiment. FIGS. 7A through 7C are schematic illustrations of different operation steps of placing the observation apparatus according to the embodiment in position at a point of observation.

When operating the observation apparatus 100 according to the present invention for observation, the pressure-resistant container closure section 111 is once removed from the pressure-resistant container main body section 110 and then, the control circuit substrate 231 and other related components are taken out. Thereafter, the picked up image data memory section 262 is made to have a sufficient memory capacity and the power supply section 240 is fully charged before the main switch 232 is turned on. Then, the BCD switch is operated for the observation sequence memory section 261 of the control circuit section to specify the total number of times of shooting. The control circuit may be made to contain an interface for an external computer (e.g., RS232C, USART or USB) so as to input information such as the number of times of shooting in the observation sequence memory section 261 by a program of the computer. Finally, the pressure-resistant container closure section 111 is closed and the photoswitch 150 and the underwater connector 160 are set to operate.

After making the observation apparatus 100 ready to work, the observation apparatus 100 is placed in position at a point of observation on the seabed by a submarine or a diver/operator as shown in FIG. 7A. Since the observation apparatus 100 is provided with the first leg section 131, the second leg section 132, the third leg section 141 and the fourth leg section 142, the observation apparatus 100 is not buried in the bottom sludge when it is placed in position on the bottom sludge in a deep sea. In other words, the observation apparatus 100 remains near the boundary of the bottom sludge and the bottom water to take a posture as shown in FIG. 7B.

As the observation apparatus 100 is placed in position to take a posture as shown in FIG. 7B, the annular elastic body 163 is taken out and the pin 152 is pulled out from the main body section of the photoswitch 150 by a diver/operator or by means of a manipulator of a submarine. Then, as a result, an observation sequence is started under the control of the control circuit contained in the pressure-resistant container main body section 110 of the observation apparatus 100. FIG. 7C illustrates this step of operation.

Figure 8:
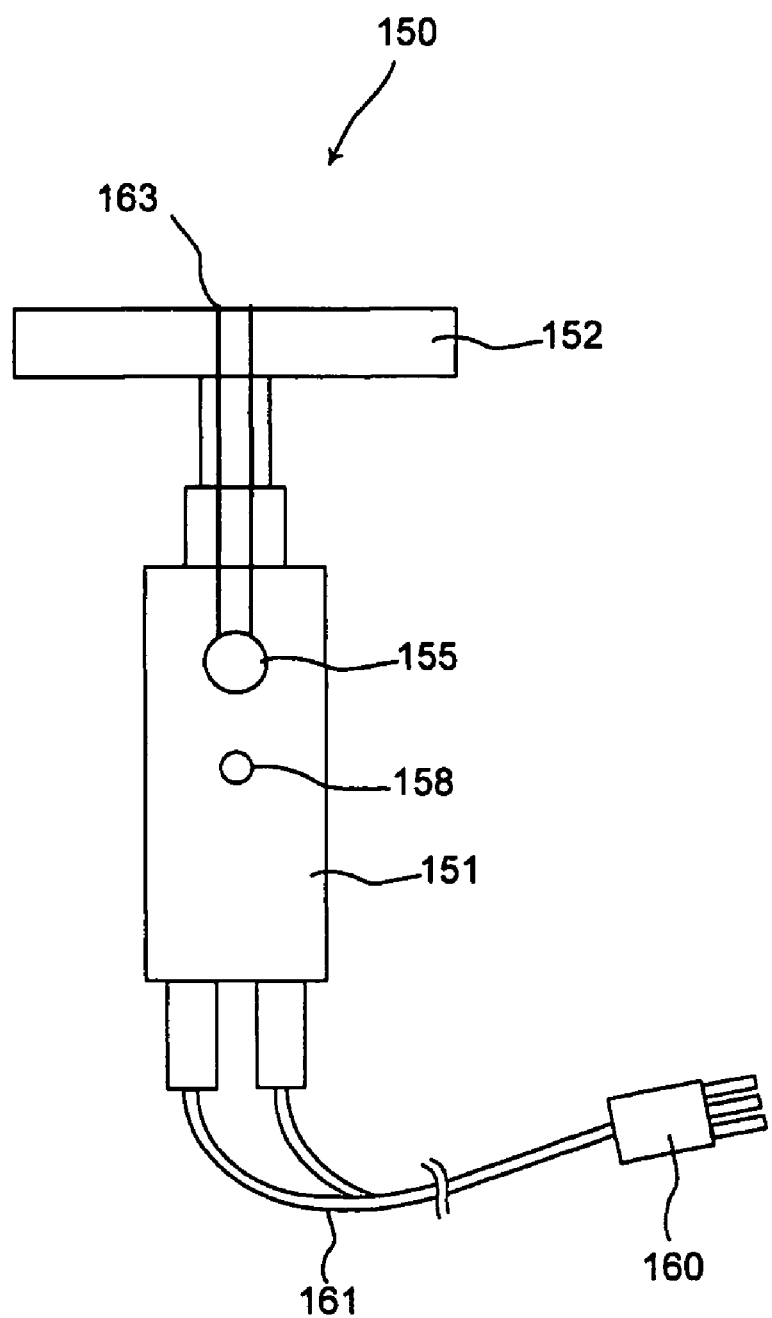
FIG. 8 is a schematic illustration of the configuration and a mode of utilization of the photoswitch of the observation apparatus according to the embodiment of the present invention.
Figure 9:
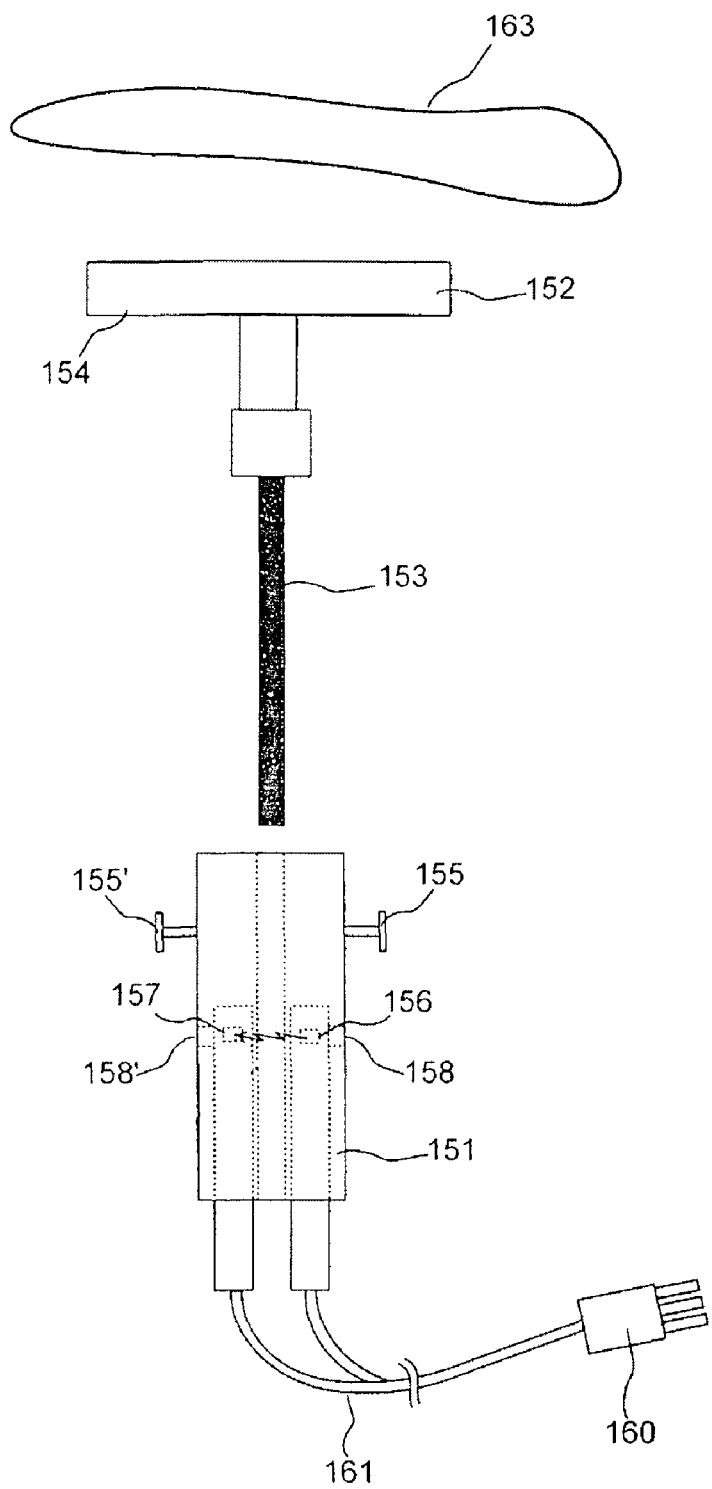
FIG. 9 is a schematic illustration of the configuration and another mode of utilization of the photoswitch of the observation apparatus according to the embodiment of the present invention.

Now, the structure and the operation of the photoswitch 150 will be described below in greater detail. FIG. 8 is a schematic illustration of the configuration and a mode of utilization of the photoswitch of the observation apparatus according to the embodiment of the present invention. FIG. 9 is a schematic illustration of the configuration and another mode of utilization of the photoswitch of the observation apparatus according to the embodiment of the present invention. In FIGS. 8 and 9, reference numerals 150, 152, 153 and 154 respectively denote the photoswitch, the pin, a light shield section and an operation section and 155, 155' denote hooks while reference numerals 156 and 157 respectively denote the light emitting element and the light receiving element, 158, 158' denote fitting/adjusting holes and 160 and 161 respectively denote the underwater connector and the cable.

The photoswitch 150 is a switch that operates as trigger for starting a real observation sequence of the observation apparatus 100 and includes a main body section of the photoswitch 150 that contains the light emitting element 156 and the light receiving element 157 and the pin 152 that is inserted into the main body section of the photoswitch 150.

The pin 152 includes the operation section 154 that serves as handle when the photoswitch 150 is operated by a driver/operator or by means of a manipulator of a submarine and the light shield section 153 arranged so as to extend from the operation section 154. Thus, the pin 152 is T-shaped as a whole as shown in FIGS. 8 and 9. The light shield section 153 of the pin 152 blocks the light path between the light emitting element 156 and the light receiving element 157 when it is fitted to the main body section of the photoswitch 150. As the pin 152 is pulled out from the main body section of the photoswitch 150 by a diver/operator or by means of a manipulator of a submarine, the light shield section 153 is taken out so that the light receiving element 157 receives light emitted from the light emitting section 156 to turn on the photoswitch 150.

The fitting/adjusting holes 158, 158' are utilized to fit the light emitting element 156 and the light receiving element 157 to the main body section of the photoswitch 150 and to adjust the fitting position of the light emitting element 156 and that of the light receiving element 157 when the light emitting element 156 and the light receiving element 157 are fitted to the main body section of the photoswitch 150 respectively. After fitting the light emitting element 156 and the light receiving element 157, the fitting/adjusting holes 158, 158' are filled with epoxy resin to seal the elements from the outside.

The hooks 155, 155' are projections to be utilized when the annular elastic body 163 is wound so as to prevent the pin 152 from coming out from the main body section of the photoswitch 150. The photoswitch 150 maintains the state where the pin 152 is inserted into the main body side of the photoswitch 150 by the resilience of the annular elastic body 163 wound around the hooks 155, 155'. FIG. 8 shows this state.

On the other hand, as the observation apparatus 100 is placed in position at a point of observation, the annular elastic body 163 is removed and the pin 152 is pulled out from the main body section of the photoswitch 150 by a diver/operator or by means of a manipulator of a submarine. As a result, the observation apparatus 100 starts an observation sequence as shown in FIG. 9 and FIG. 7C.

Now, the process that is executed when the above-described observation apparatus 100 is placed in position at a point of observation and triggered to operate by the photoswitch 150 will be described by referring to the flowcharts of FIGS. 5 and 6. Note that the process illustrated in the flowcharts of FIGS. 5 and 6 is only an exemplar mode of operation of the observation apparatus 100 and the present invention is by no means limited thereto. In other words, another mode of operation may feasibly be realized for the purpose of the present invention.

Referring to FIG. 5, the main switch 232 is turned on in Step S100 and the process of the control circuit section 250 starts. This operation is performed on the ground before placing the observation apparatus 100 in position on the seabed. Then, the pressure-resistant container closure section 111 is mounted. The pin 152 is inserted into the main body section of the photoswitch 150 and the underwater connector 160 is set to work. Then, the observation apparatus 100 is placed in position at a point of observation on the seabed as shown in FIGS. 7A and 7B.

In Step S101, it is determined if the photoswitch 150 is on or not. The process proceeds to Step S102 when the answer to the question in Step S101 is YES, whereas the process loops at Step S101 when the answer to the question in Step S101 is NO.

As the photoswitch 150 is determined to be on and the process proceeds to Step S102, a timing process is started by the timer section 252 in order to manage the observation sequence.

In Step S103, if is determined if the shooting is completed for all the number of times of shooting specified for the observation sequence or not. The process proceeds to Step S108 to end the process when the answer to the question in Step S103 is YES. On the other hand, the process proceeds to Step S104 when the answer to the question in Step S103 is NO.

In the next step, or Step S104, it is determined if the voltage of the power supply section 240 is not lower than a predetermined voltage level or not by referring to the signal from the power supply monitoring section 251. The process proceeds to Step S105 when the answer to the question in Step S104 is YES and hence power is sufficiently secured by the power supply section 240 for driving the image pickup apparatus 220.

On the other hand, the process proceeds to Step S108 to end the process at the control circuit section 250 when the answer to the question in Step S104 is NO, that is, the voltage of the power supply section 240 is lower than the predetermined voltage level and the power supply section 240 cannot secure sufficient power for driving the image pickup apparatus 220.

In Step S105, it is determined if the predetermined time period specified in the observation sequence memory section 261 has elapsed or not by referring to the timer section 252. The process loops at Step S105 when the answer to the question in Step S105 is NO, whereas the process leaves the loop and proceeds to Step S106 when the predetermined time period has elapsed and hence the answer to the question in Step S105 is YES.

The image pickup process subroutine is executed in Step S106. The process proceeds to Step S107 when the process returns from the image pickup process subroutine.

In Step S107, the reading of the counter for counting the number of times of shooting that is specified for the observation sequence is decremented by one. Subsequently, the process proceeds to Step S103.

Since the image pickup process subroutine is executed for the specified number of times as shown in the flowchart, the observation apparatus 100 according to the present invention can observe temporal fluctuations of the two-dimensional distribution of oxygen concentration in the bottom sludge on the seabed and also in the seawater.

Now, the image pickup process subroutine will be described below by referring to FIG. 6. Referring to FIG. 6, as the image pickup process subroutine is started in Step S200, the subroutine proceeds to Step S201, where the excitation light sources 210, 211 are turned on so that the pigment of the oxygen quenching material in the sensor foil 200 is excited by excitation light to emit light.

Subsequently, in Step S202, the shutter of the image pickup apparatus 222 is opened to start exposure. In Step S203, it is determined if the predetermined exposure time period stored in the observation sequence memory section 261 has elapsed or not. The subroutine loops at Step S203 when the answer to the question in Step S203 is NO, whereas the subroutine proceeds to Step S204 when the answer to the question in Step S203 is YES.

In Step S204, the shutter of the image pickup apparatus 222 is closed to end the exposure. In the next step, or Step S205, the excitation light sources 210, 211 are turned off. In Step S206, the process of storing the picked up image data in the picked up image data memory section 260 is executed. In the next step, or Step S207, the subroutine returns to the main routine.

Figure 10:
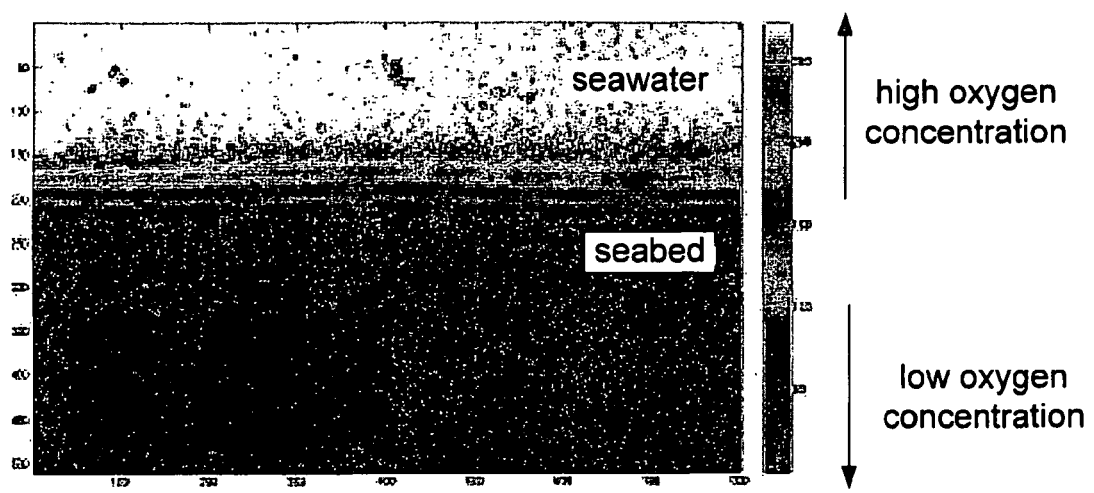
FIG. 10 is a schematic illustration of an exemplar observation of the oxygen concentration distribution along the boundary of the bottom sludge and the bottom water made by the observation apparatus according to the embodiment of the present invention.

An example of picked up image data that can be acquired by the above-described observation apparatus 100 will be shown in FIG. 10. FIG. 10 is a schematic illustration of an exemplar observation of the oxygen concentration distribution along the boundary of the bottom sludge and the bottom water made by the observation apparatus of this embodiment. The example of FIG. 10 is produced by processing the picked up image data stored in the picked up image data memory section 260 so as to make the viewer easily grasp the oxygen concentration distribution.

Thus, with the above-described observation apparatus 100 of this embodiment, it is possible to observe the temporal fluctuations of the two-dimensional distribution of oxygen concentration in the bottom sludge and the bottom water on the seabed.

Figure 11:
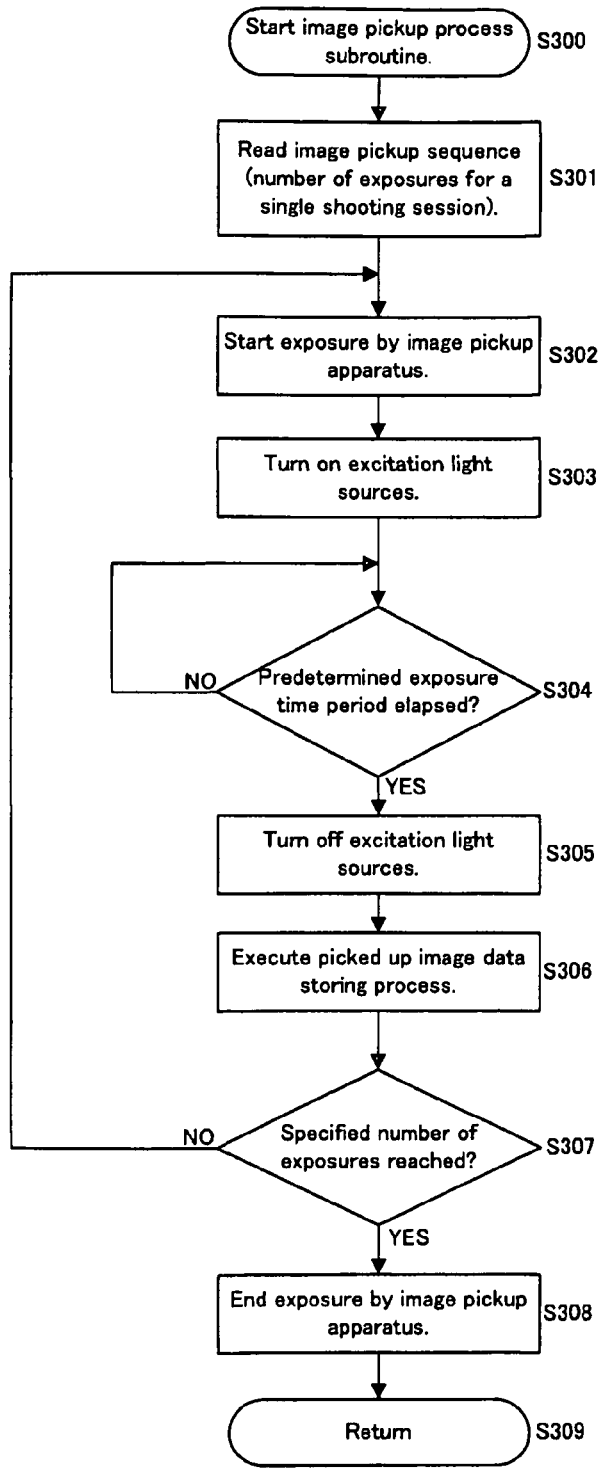
FIG. 11 is a flowchart of the image pickup process subroutine of the control circuit of an observation apparatus according to another embodiment of the present invention.

Various image pickup process subroutines can be conceivable for Step S106 in FIG. 5. Therefore, another embodiment of the present invention will be described below in terms of image pickup process subroutine by referring to FIG. 11. FIG. 11 is a flowchart of the image pickup process subroutine of the control circuit of another embodiment of observation apparatus according to the present invention. With the image pickup process subroutine of this embodiment, picked up image data of several shootings are acquired by a single image pickup process subroutine.

Referring to FIG. 11, as the image pickup process subroutine is started in Step S300, it proceeds to Step S301, where the observation sequence and the number of exposures in a single shooting session are read from the observation sequence memory section 261. Thus, there may be a plurality of exposures in a single shooting session. When a single shooting session includes a plurality of exposures, the average value of a set of values obtained by the plurality of exposures can be obtained in a subsequent data processing step to improve the accuracy of the oxygen concentration image to be produced.

Subsequently, in Step S302, the shutter of the image pickup apparatus 222 is opened to start exposure. Then, in Step S303, the excitation light sources 210, 211 are turned on so that the pigment of the oxygen quenching material in the sensor foil 200 is excited by excitation light to emit light. In the next step, or Step S304, it is determined if the predetermined exposure time as stored in the observation sequence memory section 261 has elapsed or not. The subroutine loops at Step S304 when the answer to the question in Step S304 is NO, whereas it proceeds to Step S305 when the answer to the question is YES. In Step S305, the excitation light sources 210, 211 are turned off. Then, in the next step, or Step S306, the picked up image data are stored in the picked up image data memory section 260.

Thereafter, in Step S307, it is determined if the number of exposures specified in the image pickup sequence has been reached or not. The subroutine proceeds to Step S303 for the remaining exposure(s) when the answer to the question in Step S307 is NO, whereas the subroutine proceeds to Step S308 when the answer to the question in Step S307 is YES so as to close the shutter of the image pickup apparatus 222 and return to the main routine in the next step, or Step S309.

With the above-described embodiment of the present invention, a single shooting session includes a plurality of exposures to obtain picked up image data so that the average value of a set of values obtained by the plurality of exposures can be obtained in a subsequent data processing step to improve the accuracy of the oxygen concentration image to be produced.

Additionally, with the above-described embodiment of the present invention, the shutter of the image pickup apparatus 222 is opened and the excitation light sources 210, 211 are turned on to excite the pigment of the oxygen quenching material in the sensor foil 200. Then, when it is determined that the predetermined exposure time has elapsed, the excitation light sources 210, 211 are turned off and a process of acquiring the picked up image data of a single exposure is executed. The duration of an exposure can be controlled accurately by controlling the duration of excitation of the excitation light sources 210, 211 rather than by directly controlling the duration of an exposure with use of the shutter. Therefore, this embodiment can acquire accurate and reliable data. No problem arises when the excitation light sources 210, 211 are turned on to emit excitation light after the shutter of the image pickup apparatus 222 is opened because a shooting operation is started without light.

What is claimed is:

1. An observation apparatus for surveying the distribution of oxygen concentration near the bed of a body of water, comprising:
   a pressure-resistant container main body section that has a pressure-resistant window and is hermetically sealed by a pressure-resistant container closure section, said pressure-resistant container closure section is located at one end of the pressure-resistant container main body section of said observation apparatus;
   a sensor foil that contains an oxygen quenching material, said sensor foil is arranged to an outside of the pressure-resistant window located at an end opposite to said one end of the pressure-resistant container main body section of said observation apparatus, wherein said sensor is arranged only on the outside of the pressure-resistant window;

an excitation light source that is arranged at the pressure-resistant container main body section to irradiate the sensor foil;
an image pickup apparatus that shoots the sensor foil; and
a plurality of leg sections to position the observation apparatus near the boundary of the bed of said body of water without burying the observation apparatus in the bed of said body of water so as to allow the observation apparatus to observe temporal changes in the oxygen concentration distribution at the boundary of the bed of said body of water.

2. The apparatus according to claim 1, wherein
a switch is arranged on the outer periphery of the pressure-resistant container main body section and an observation sequence is started by the switch.

3. The apparatus according to claim 1 or 2, wherein
a control circuit is arranged in the inside of the pressure-resistant container main body section to control the excitation light source and the image pickup apparatus.

4. The apparatus according to claim 3, wherein
a main switch is arranged in the inside of the pressure-resistant container main body section to turn on and off the power supply to the control circuit.

5. The apparatus according to claim 1, wherein
said body of water includes oceans, rivers, lakes or swamps.

* * * * *